United States Patent [19]
Koji

[11] Patent Number: 5,039,865
[45] Date of Patent: Aug. 13, 1991

[54] SANITATION APPARATUS

[75] Inventor: Masashi Koji, Tokyo, Japan

[73] Assignee: Hoshin Kagaku Sangyosho Co., Ltd., Tokyo, Japan

[21] Appl. No.: 449,928

[22] PCT Filed: Jan. 26, 1989

[86] PCT No.: PCT/JP89/00073
§ 371 Date: Sep. 19, 1989
§ 102(e) Date: Sep. 19, 1989

[87] PCT Pub. No.: WO89/06981
PCT Pub. Date: Aug. 10, 1989

[30] Foreign Application Priority Data
Jan. 27, 1988 [JP] Japan .................. 63-16274

[51] Int. Cl.$^5$ .............................. A61L 2/10
[52] U.S. Cl. .................. 250/455.1; 250/436; 250/432 R; 250/435; 422/22; 422/307
[58] Field of Search .......... 250/455.1, 454.1, 436, 250/432 R, 435; 422/24, 22, 295, 307; 210/748

[56] References Cited
U.S. PATENT DOCUMENTS
4,899,057 2/1990 Koji .................. 250/455.1

FOREIGN PATENT DOCUMENTS
61-293373 12/1986 Japan .

Primary Examiner—Jack I. Berman
Assistant Examiner—Kiet T. Nguyen
Attorney, Agent, or Firm—Bauer & Schaffer

[57] ABSTRACT

A sanitation apparatus of this invention is arranged such that a far-infrared ray emitting member (5) made of ceramics, metal oxide or the like is provided to emit far-infrared rays to prevent proliferation of bacteria or to sterilize objects (1, 11, 12, 15, 19) to be kept in a sanitized condition, wherein the far-infrared ray emitting member is heated to emit far-infrared rays which irradiate the object so that proliferation of bacteria is prevented or bacteria is sterilized, and in which a temperature of the far-infrared ray emitting member is kept in a range of about 30° C. to 60° C. so as to prevent a temperature of the object from being increased too much. Thus, the apparatus can be made compact in size and inexpensive, and heating energy can be saved. Also, the application field of the apparatus can be extended, and a bad influence of temperature exerted upon the objects such as when the objects are burned can be prevented, and a risk that the user will be burned by the objects heated too much can be avoided.

3 Claims, 2 Drawing Sheets

1

SANITATION APPARATUS

TECHNICAL FIELD

This invention relates to a sanitation apparatus for use with a tank containing liquid to be sanitized or from which the liquid sanitized is supplied, receptacles containing tooth brush and comb, food service utensils, hospital service utensils, barbers and beauty parlors business utensils, utensils for sauna bath and recreation facilities to be sanitized, nozzle and water purifier for supplying sterilized water and drinking water or the like, filter itself, pipes for supplying various kinds of beverages sterilized, pipes for transporting air, gas, liquid or powder, a stirring apparatus therefor, sterilization of telephone set including transmitter and receiver to be sanitized and sterilization of toilet seat, sterilization of wet towel and laundry, sterilization of dried cereals, utilization for cleaners for sterilizing ticks, virus and bacteria, utilization for sterilizing bacteria and the like within a cooling tower, sterilization of sauna bath, bath, shower room and kitchen of high temperature, sterilization of door knob, sterilization of the surfaces of push buttons, sterilization of footwears and sterilization of medicines, foods and beverages contained in receptacles pervious to far-infrared rays.

BACKGROUND ART

There has been known so far such a method which comprises the steps of placing an object to be sanitized into an infrared ray irradiating apparatus in which a ceramic heater is provided as an infrared ray irradiation body and operating the ceramic heater to irradiate the object with infrared rays containing plenty of far-infrared rays while ventilating the air within the infrared ray irradiating apparatus, thereby heat-sterilizing the object (Japanese Laid-Open Patent Gazette No. 50-685).

The above-noted prior-art apparatus utilizes the ceramic heater as the infrared ray irradiating bodies so that a heating temperature is as high as, for example, 100° to 450° C. Such high temperature exerts a harmful influence upon the object to be sanitized, causing the object to be sanitized to be burned. Therefore, the ceramic heater and the object to be sanitized must be cooled by air and water, which provides a large-sized and expensive apparatus.

It is frequently observed that the large-sized apparatus heats extra portion of the object to be sanitized. This is uneconomical and makes the temperature administration difficult. Further, the ceramic heater can not directly oppose the object to be sanitized or can not be placed closest to the object to be sanitized, which limits the application field of the sanitation device. Furthermore, the temperature exerts a harmful influence upon the object to be sanitized so that the object to be sanitized is damaged by burning or the object to be sanitized is heated too much. There is then a risk that the user will be burned.

DISCLOSURE OF INVENTION

In view of the above-noted aspect, the present invention is to provide a sanitation apparatus which can eliminate the above-mentioned defects.

The sanitation apparatus of this invention comprises a far-infrared ray emitting member 5 made of ceramics, metal oxide or the like for emitting far-infrared rays to prevent increase of germ or to sterilize in association with an object to be sanitized and a heating member 10 which heats the far-infrared ray emitting member 5 to emit far-infrared rays, which are applied to the object to be sanitized to prevent increase of germ or to sterilize the object to be sanitized and the temperature of the far-infrared ray emitting member 5 is kept in a range of from about 30° C. to 60° C. so that the temperature of the object may not increase excessively. In other words, the far-infrared ray emitting member 5 is provided in association with the object to be sanitized. The far-infrared ray emitting member 5 is heated at about 30° C. to 60° C. by, for example, the power source 10 to apply much far-infrared rays to the object to be sanitized so that increase of germ is prevented or that the object to be sanitized is sterilized. Thus, the sanitation apparatus can be made compact in size and inexpensive, energy for heating can be saved and the application field of the sanitation apparatus can be extended. Further, the harmful influence of temperature upon the object to be sanitized can be avoided and the above-noted risk can be avoided.

BEST MODE FOR CARRYING OUT THE INVENTION

The respective embodiments of this invention will hereinafter be described in detail with reference to FIGS. 1 to 5.

Figure 1:
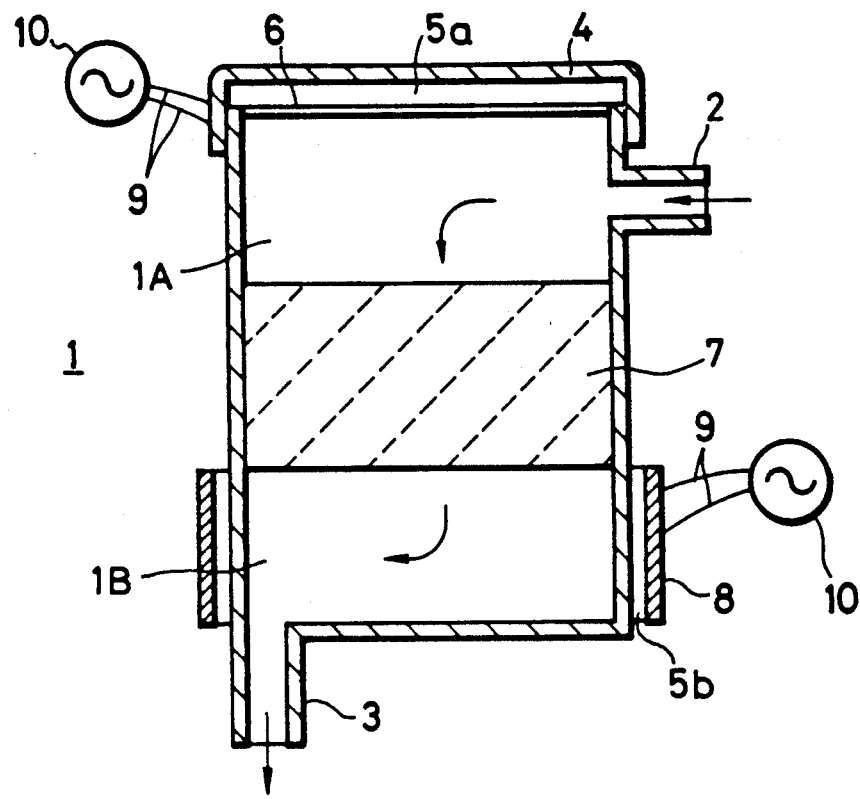
FIG. 1 is a diagrammatic view of a section illustrating a first embodiment of the present invention.

FIG. 1 is a diagrammatic view of a section illustrating a first embodiment in which this invention is applied to a purifier. In the same figure, reference numeral 1 generally designates a washing apparatus, 2 a water inlet, 3 a water outlet, 4 a cover, 5 a far-infrared ray emitting member made of, for example, ceramics, metal oxide or a mixture of ceramics and metal oxide, 6 a permeable film pervious to far-infrared rays, 7 a water filter, 8 an outside base plate for the far-infrared ray emitting member 5, 9 lead wires and 10 a power supply source. Such water purifier 1 can be regarded as a kind of small tank. The outward form of this tank 1 may be columnar or prismatic, and the cover 4 may be either circular or rectangular depending on the columnar or prismatic outward form of the tank. The far-infrared ray emitting member 5 and the permeable film 6 are secured to the rear side of the cover 4. The far-infrared ray emitting member 5 is heated, for example, to 38° C. by the power supply source 10 through the lead wires 9 to emit far-infrared rays. The far-infrared rays are applied to the inlet side (primary side) of the filter 7. The outside base plate 8 is either annular or rectangular ring-shaped depending on the columnar or prismatic outward form of the tank. The far-infrared ray emitting member 5, secured to the inside of the outside base plate 8, is heated to, for example, 38° C. by the power supply source 10 through the lead wires 9 to apply far-infrared rays to the outlet side (secondary side) of the filter 7.

In this embodiment, at least the tank portion to which the far-infrared ray emitting member 5 is located via the base plate 8 must be made of a material pervious to far-infrared rays. If the far-infrared ray emitting member 5 is provided only at the rear side of the cover 4, the tank will not be made of a material pervious to far-infrared rays. The filter 7 may be a far-infrared ray emitting member. If this far-infrared ray emitting member is used without other far-infrared ray emitting members, it is heated by another power supply source or liquid or air passing through the far-infrared emitting member 5 heated to 30° C. to 60° C. The film 6 pervious to far-infrared rays may be removed as required.

As described above, according to this embodiment, the far-infrared ray emitting member 5 is heated by the power supply source 10 and generates far-infrared rays to avoid the increase of germ or to promote the sterilization of bacteria.

Figure 2:
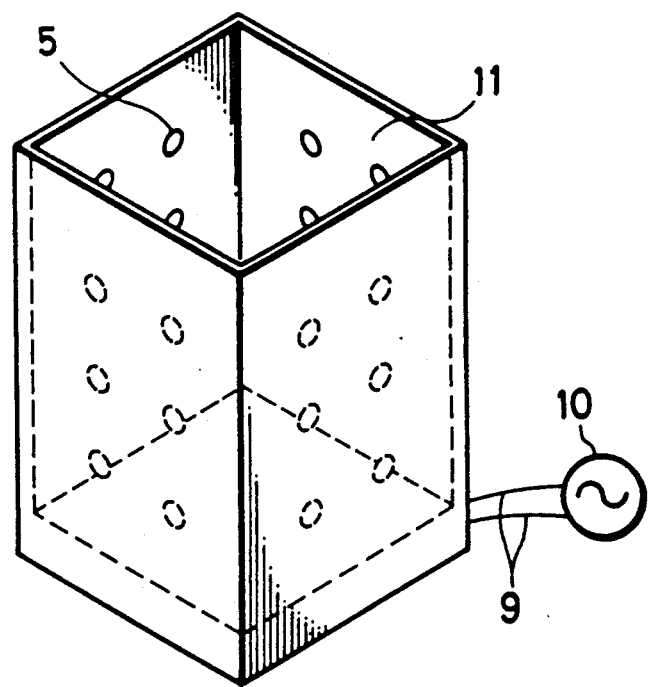
FIG. 2 is a perspective view illustrating a second embodiment of the present invention.

FIG. 2 is a perspective view illustrating a second embodiment in which the present invention is applied to a rectangular receptacle. In the figure, reference numeral 11 designates a receptacle. A plurality of far-infrared ray emitting members 5, each being a grain shape, are arranged on the base plates (not shown) provided on the inside walls of the receptacle 11, and each are connected to the power supply source 10. The receptacle 11 may accommodate therein, in addition to a tooth brush and a comb, a glass, a cap of microphone or food service utensils which will touch the user's mouth, hospital sanitation utensils, beauty shop utensils, utensils used in sauna bath and recreation facilities, etcetera. If the products to be accommodated in the receptacle are made of material pervious to far-infrared rays, more powerful effects can be achieved. While in the illustrated embodiment the far-infrared ray emitting members 5 are arranged on the inner side walls of the receptacle 11, they may be provided on the bottom wall. While in this embodiment the far-infrared ray emitting members 5 are provided on the four inside walls of the receptacle 11, they may be provided at least on one inside wall of the receptacle.

The plurality of grain-shaped far-infrared ray emitting members 5 may be replaced with the whole surface of at least one inside wall of the receptacle 11 which is made as a far-infrared ray emitting member.

In this manner, according to this embodiment, the far-infrared ray emitting members 5 provided on the inner walls of the receptacle 11 are heated, for example, to 38° C. by the power supply source 10 to emit far-infrared rays, thereby preventing the increase of germ or promoting the sterilization.

Figure 3:
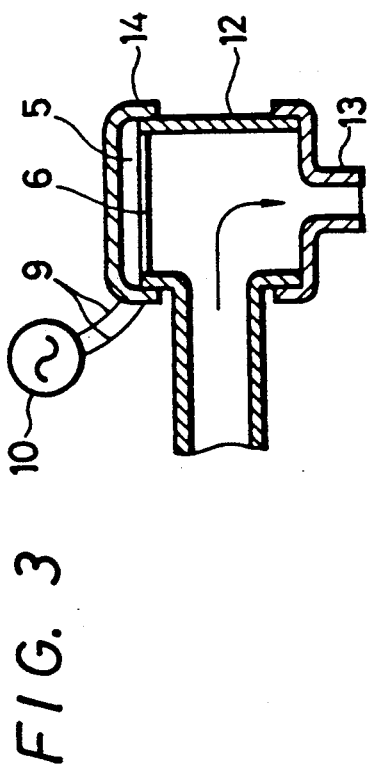
FIG. 3 is a diagrammatic view of a section illustrating a third embodiment of the present invention.

FIG. 3 is a diagrammatic view of a section illustrating a third embodiment in which this invention is applied to a nozzle. In the figure, reference numeral 12 designates a nozzle which supplies a drinking water or a sterilized water, 13 a nozzle mouth capping the top of the nozzle, 14 a capping member formed as one body with the far-infrared ray emitting member 5 and the film 6 pervious to far-infrared rays. While in this embodiment the capping member 14 is not necessarily made of material pervious to far-infrared rays, the nozzle mouth 13, made of material pervious to far-infrared rays, is attached to the top of the nozzle 12. The nozzle mouth 13 may be formed as a shower-head type having a number of small apertures. Further, it may be possible that the far-infrared ray emitting member 5 is removed and the nozzle mouth 13 is formed as the far-infrared ray emitting member which is heated by the power supply source 10.

Alternatively, the nozzle mouth 13 is not directly heated by the power supply source 10 but is heated by induced heat or water heated by a heating source provided at the inlet (left-hand side) of the nozzle 12.

Also in this embodiment, the far-infrared ray emitting member 5 is heated, for example, to 38° C. by the power supply source 10 to emit far-infrared rays, thereby preventing proliferation of bacteria or promoting the sterilization.

Figure 4:
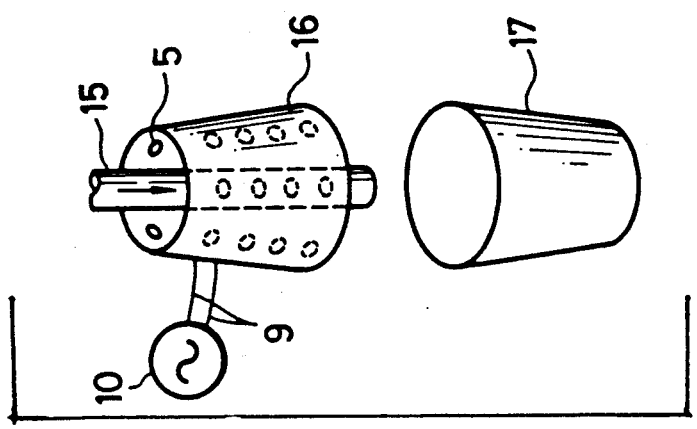
FIG. 4 is a perspective view illustrating a fourth embodiment of the present invention.

FIG. 4 is a perspective view illustrating a fourth embodiment in which this invention is applied to a nozzle. In this embodiment, the present invention is applied to a nozzle 15 long in the longitudinal direction and which is made of a material pervious to far-infrared rays. A plurality of far-infrared ray emitting members 5, each having a configuration of, for example, a grain, are arranged on the inside wall of an inverted-glass-shaped base plate 16, and this base plate is fitted to the top of the nozzle 15 by some suitable means. Each of the far-infrared ray emitting members 5 is heated, for example, to 38° C. to 42° C. by the power supply source 10 via the lead wires 9, respectively. In this embodiment, the far-infrared rays can be applied not only to the outlet of the nozzle 15 but also to the peripheral portion and the inside of a glass 17 located above or below the nozzle.

As described above, also in accordance with this embodiment, the far-infrared ray emitting members 5 are heated by the power supply source 10 to generate far-infrared rays, thereby preventing proliferation of bacteria or promoting the sterilization.

Figure 5:
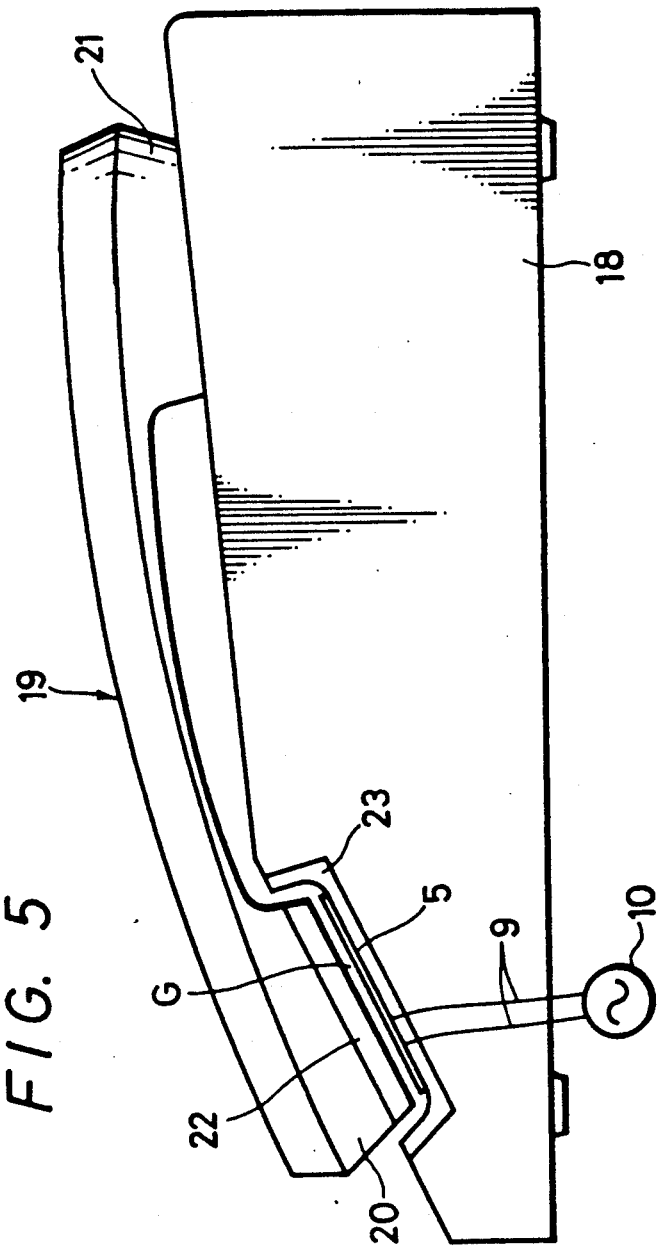
FIG. 5 is a side view illustrating a fifth embodiment of the present invention.

FIG. 5 is a side view illustrating a fifth embodiment in which this invention is applied to a telephone set. In the figure, reference numeral 18 designates a telephone set, 19 a handset, 20 a transmitter forming one side of the handset 19, 21 a receiver forming the other side of the handset 19, 22 a receiver cover detachably attached to the top of the transmitter 20 and 23 a supporting portion secured to the telephone set 18 to support the transmitter 20.

The far-infrared ray emitting member 5 is provided on the bottom of the supporting portion 23. The transmitter 20 is made slightly distant from the supporting portion 23 to form a gap G as shown in the figure so that the far-infrared rays from the far-infrared ray emitting member 5 can be effectively applied to the receiver cover 22. To this end, the telephone set side is provided with a protrusion for supporting the transmitter 20, though not shown.

It may be possible that the transmitter 20 side is arranged to incorporate therein the far-infrared ray emitting member 5. At that time, the receiver cover 22 is made of material pervious to far-infrared rays, so that it is needless to provide the gap G. Further, the above countermeasure may be incorporated not only in the transmitter 20 side but also in the receiver 21 side. The far-infrared ray emitting member 5 is heated, for example, to 38° C. to 42° C. by the power supply source 10 via the lead wires 9 as described above.

Since in the portion to which the far-infrared rays are applied from the far-infrared ray emitting member 5 which is heated by the power supply source 10 proliferation of bacteria is suppressed or sterilization is carried out, the transmitter-receiver can be kept in a sanitary condition.

While the present invention is applied to the telephone set in the fifth embodiment, the present invention can similarly be applied to other ones such as a microphone and an inter-phone by which the user can make conversation.

While the far-infrared ray emitting member 5 is heated by the power supply source 10 in the above-mentioned respective embodiments, it may be heated by using a heating material which generates heat by means of friction or chemical reaction of water and lime. Alternatively, the far-infrared ray emitting member may be heated by the irradiation of light, hot water, hot air or the like. Further, the temperature at which the far-infrared ray emitting member 5 is not limited to the above-noted values but it may fall in a range of about 30° to 60° C. so long as a bad influence can be prevented from being exerted upon the object to be sanitized such as when the object is burned.

The following table illustrates examples of sterilization data by means of the far-infrared ray emitting member 5 heated. It is thus apparent therefrom that almost all of bacteria can be sterilized.

| Irradiation time of far-infrared ray emitting member | Heating temperature | Name of germs | Sterilization ratio |
| --- | --- | --- | --- |
| 5 minutes | 36° C. | bacillus subtilis | 86% |
| 5 minutes | 40° C. | bacillus subtilis | 99% |
| 5 minutes | 46° C. | bacillus subtilis | 99.9% |
| 2 minutes | 56° C. | bacillus subtilis | 99.99% |
| 1 minutes | 56° C. | bacillus subtilis | 99% |
| 1 minutes | 43° C. | escherichia coli | 99.99% |
| 1 minutes | 59° C. | bacillus subtilis spores | 99% |
| 3 minutes | 57° C. | aspergillus niger | 99.9% |

As set forth above, according to the present invention, since the far-infrared ray emitting member made of a ceramic material, a metal oxide or the like is heated at a temperature of about 30° C. to 60° C. to emit far-infrared rays which irradiate the object to prevent the proliferation of bacteria or to sterilize the germs, so that the prior art air-cooling means, water-cooling means and so on are not required and hence, the sanitation apparatus can be made compact in size and also inexpensive in cost. Further, since the unnecessary portion of the object is not irradiated, the heating energy can be saved and the temperature administration can be made with ease. Further, since the far-infrared ray emitting member is directly opposed to or is located at the position nearest to the object, the present invention can be applied to various kinds of products and the field of its application can be increased. Furthermore, since the far-infrared ray emitting member can be kept at a relatively low temperature in order that the temperature of the object can be prevented from being increased considerably, a bad influence of temperature can be prevented from being exerted upon the object, thus the object being prevented from being burned or the like. Hence, it is possible to avoid a risk that the user will be burned at the finger when the user picks up the headted object thus sterilized.

I claim:

1. Apparatus for sanitizing objects comprising a far-infrared ray emitter made of material selected from ceramic, metal oxide and mixtures thereof, means for locating said far-infrared ray emitter in close proximity to the object to be sanitized and heating means for maintaining the far-infrared emitter at a temperature between 30 degrees and 49 degrees centigrade so as to avoid overheating said object and preventing growth of bacteria thereon.

2. The apparatus according to claim 1, wherein said objects are contained in a surrounding enclosure made of material not pervious to infrared radiation and the far-infrared emitter is located on at least one wall.

3. A method for sanitizing objects comprising the steps of providing a far-infrared emitter made of material selected from ceramic, metal oxide and mixtures thereof, locating said emitter in close proximity to the object to be sanitized and maintaining the emitter at a temperature of between 30 degrees and 49 degrees centigrade while irradiating the object.

* * * * *